United States Patent
Holt et al.

(10) Patent No.: US 10,383,814 B2
(45) Date of Patent: Aug. 20, 2019

(54) HONEY COMPOSITIONS

(71) Applicant: Honeylab Limited, Karaka Bays, Wellington (NZ)

(72) Inventors: Shaun Lister Holt, Tauranga (NZ); Laurence Greig, Wellington (NZ)

(73) Assignee: Honeylab Limited, Wellington (NZ)

( * ) Notice: Subject to any disclaimer, the term of this patent is extended or adjusted under 35 U.S.C. 154(b) by 573 days.

(21) Appl. No.: 14/916,126

(22) PCT Filed: Aug. 26, 2014

(86) PCT No.: PCT/NZ2014/000175
§ 371 (c)(1),
(2) Date: Mar. 2, 2016

(87) PCT Pub. No.: WO2015/030605
PCT Pub. Date: Mar. 5, 2015

(65) Prior Publication Data
US 2016/0193141 A1    Jul. 7, 2016

Related U.S. Application Data

(60) Provisional application No. 61/872,799, filed on Sep. 2, 2013.

(51) Int. Cl.
| *A01N 65/00* | (2009.01) |
| *A61K 8/98* | (2006.01) |
| *A61K 35/644* | (2015.01) |
| *A61K 8/34* | (2006.01) |
| *A61Q 19/00* | (2006.01) |
| *A23L 21/25* | (2016.01) |

(52) U.S. Cl.
CPC ............... *A61K 8/988* (2013.01); *A61K 8/345* (2013.01); *A61K 35/644* (2013.01); *A61Q 19/00* (2013.01); *A23L 21/25* (2016.08)

(58) Field of Classification Search
CPC ....................................................... A61K 36/00
USPC ......................................................... 424/725
See application file for complete search history.

(56) References Cited

U.S. PATENT DOCUMENTS

| 2004/0054313 A1 | 3/2004 | Molan |
| 2013/0045224 A1 | 2/2013 | Sims et al. |

FOREIGN PATENT DOCUMENTS

| CN | 1285185 | * | 2/2001 |
| CN | 1899262 A | | 1/2007 |
| NZ | 501687 A | | 8/2002 |
| NZ | 542258 A | | 5/2010 |
| WO | 2007045931 A2 | | 4/2007 |
| WO | 2007137369 A1 | | 12/2007 |
| WO | 2011046454 A1 | | 4/2011 |
| WO | 2014076639 A1 | | 5/2014 |

OTHER PUBLICATIONS

Allen, K.L., et al., "A survey of the antibacterial activity of some New Zealand honeys," 1991, J Pharma Pharmacol, 43/12:817-822.
Elewski, B.E., et al., "A comparison of 15% azelaic acid gel and 0.75% metronidazole gel in the topical treatment of papulopustular rosacea: results of a randomized trial," 2003, Archives of Dermatology 139/11:1444-150. (Downloaded from http://archderm.jamanetwork.com Aug. 17, 2015).
Finlay, A.Y., et al., "Dermatology Life Quality Index (DLQI)—a simple practical measure for routine clinical use," 1994, Clin Exp Dermatol., 19:210-216.
Gannabathula, S., et al., "Arabinogalactan Proteins Contribute to the Immunostimulatory Properties of New Zealand Honeys," 2012, Immunopharmacology and Immunotoxicology, 34/4:598-607.
Holt, S., et al., "New Zealand Kanuka Honey has High Levels of Methylglyoxal and Antimicrobial Activity," 2012, J Complementary and Alternative Medicine, 18/3:203-204.
International Search Report dated Oct. 27, 2014, in PCT/NZ2014/000175, 5 pages.
Written Opinion dated Oct. 27, 2014, in PCT/NZ2014/000175, 5 pages.
Braithwaite, I., et al., "Randomised Controlled Trial of Topical Kanuka Honey for the Treatment of Rosacea," 2015, BMJ Open, 5:e007651, 7 pages.

* cited by examiner

*Primary Examiner* — Michael V Meller
(74) *Attorney, Agent, or Firm* — Stinson LLP

(57) ABSTRACT

This invention relates generally to compositions comprising honey and glycerine, methods for preparing such compositions and their use for the treatment or prevention of skin diseases such as acne, rosacea, nappy rash, or those caused by herpes simplex virus 1 or herpes simplex virus 2.

16 Claims, No Drawings

HONEY COMPOSITIONS

REFERENCE TO RELATED APPLICATIONS

This application is the 371 National Stage Application based on International Application Serial No. PCT/NZ2014/000175, filed Aug. 26, 2014, and claims the benefit of U.S. Provisional Application Ser. No. 61/872,799, filed Sep. 2, 2013, the entire contents of which are incorporated herein by reference.

FIELD OF INVENTION

This invention relates generally to compositions comprising honey and glycerine, methods for preparing such compositions and their uses.

BACKGROUND

Honey has been used for centuries to treat skin conditions and is known historically for its effectiveness in the treatment of wounds and burns.

In recent times, manuka honey, in particular, has received attention for its reported antibacterial activity. This honey is produced by bees who harvest the nectar of *Leptospermum scoparium*. The antibacterial activity of manuka honey has been labelled the "Unique Manuka Factor" (UMF) and it has been reported that the UMF derives from the presence of methylglyoxal in the honey.

WO 2007/137369 describes medicinal compositions containing honey derived from *Leptospermum scoparium* and their use in treating ophthalmic, respiratory or otic conditions caused by microbial infections.

Kanuka honey, on the other hand, is a bio-active honey that is less well-known than manuka honey. It is produced by bees who harvest the nectar of the kanuka (*Kunzea ericoides*) and has been found to have anti-microbial activity against *Staphylococcus aureus*. Furthermore, raw kanuka honey has been reported to have methylglyoxal levels of about 1024 mg/kg and medical grade kanuka honey has been reported to have methylglyoxal levels of 1154 mg/kg (S Holt et al., The Journal of Complementary and Alternative Medicine, (2012) 18(3), 203-204).

There are difficulties associated with the use of honey as a skin treatment. Honey itself is sticky and strong smelling. The consistency of honey varies with temperature. For example, at room temperature honey might be a of suitable consistency for application to the skin, but at lower temperatures, such as a normal household refrigeration temperature of about 4° C., honey can become hard and can crystallise, which reduces its ease of use and appeal to users. In warmer conditions, its viscosity decreases and honey can become too "runny" for application to skin.

Some efforts have been made in formulating honeys, e.g. for wound treatment. NZ 542258 describes a manuka honey composition for treating wounds. The composition includes a viscosity increasing agent which increases, or at least maintains, the viscosity of the composition after application to a wound. NZ501687 describes a wound dressing composition that includes honey and one or more gelling agents, such as alginate-based materials.

However, while formulating honey with other additives might address some of the difficulties associated with using honey as a skin treatment, dilution of the honey can result in the loss of its particular biological activity (e.g. see S Holt et al., The Journal of Complementary and Alternative Medicine, (2012) 18(3), 203-204).

There is therefore a need for honey compositions that are stable at a variety of temperatures, and wherein the honey retains its biological activity.

It is an object of the invention to provide a composition comprising honey and glycerine, and methods for preparing such compositions, that overcome some of these problems, or to at least provide a useful alternative.

STATEMENTS OF INVENTION

In a first aspect, the invention provides a honey composition comprising:
from about 85% w/w honey to about 95% w/w honey; and
from about 5% w/w glycerine to about 15% w/w glycerine.

In a second aspect the invention provides a method of preparing a honey composition including the step of admixing honey with glycerine, at a ratio of honey to glycerine of about 85% honey:15% glycerine to about 95% honey:5% glycerine (w/w).

Preferably the honey is a bio-active honey, more preferably it is kanuka honey. Alternatively, the honey may be a mixture of bio-active honeys, e.g. a mixture of manuka and kanuka honeys. Still more preferably the honey is medical grade kanuka honey.

Preferably the honey composition comprises about 90% w/w honey and about 10% w/w glycerine.

Preferably the honey composition is substantially free of other components. Alternatively, the honey composition may further comprise one or more additional components.

In a further aspect, the invention provides a honey composition comprising:
honey and glycerine in a ratio of about 85:15 to about 95:5 honey to glycerine; and
one or more additional components.

Preferably the ratio of honey to glycerine is about 90:10 honey to glycerine. The one or more additional components may be, for example, one or more bio-active compounds, e.g. one or more drug compounds. The one or more additional components may be, for example, one or more medicaments useful for treating a skin disorder.

It is further preferred that the honey composition is stable when stored at temperatures below room temperature, e.g. between about 4° C. and about 10° C., e.g. at a temperature of about 4° C., for up to 8 days. It is also preferred that sugars present in the honey composition do not crystallise when the honey composition is stored at temperatures below room temperature, e.g. between about 4° C. and about 10° C., e.g. at a temperature of about 4° C., for up to 8 days.

It is further preferred that the honey composition is stable when stored at temperatures above room temperature, e.g. between about 20° C. and about 35° C., e.g. at temperatures of about 35° C., for up to 15 days.

It is further preferred that the honey composition has a total activity against *Staphylococcus aureus* NZRM 87 (ATCC 9144), and expressed as equivalent ° A) phenol, of at least about 18% phenol, preferably at least about 21% phenol, more preferably about 21-22% phenol, most preferably about 21.8% phenol.

In a third aspect, the invention provides a method of improving the temperature stability of a honey, including the step of admixing honey with glycerine, at a ratio of honey to glycerine of about 85% honey:15% glycerine to about 95% honey:5% glycerine (w/w).

Preferably the honey is a bio-active honey, more preferably it is kanuka honey. Alternatively, the honey may be a mixture of bio-active honeys, e.g. a mixture of manuka and kanuka honeys. Still more preferably the honey is medical grade kanuka honey.

Preferably the ratio of honey to glycerine is about 90% honey:10% glycerine (w/w).

The invention also provides a stable honey composition produced according to the method of the third aspect of the invention. It is preferred that the stable honey composition is stable when stored at temperatures between about 4° C. and about 10° C., e.g. at a temperature of about 4° C., for up to 8 days. It is also preferred that sugars present in the stable honey composition do not crystallise when the honey composition is stored at temperatures between about 4° C. and about 10° C., e.g. at a temperature of about 4° C., for up to 8 days. It is further preferred that the stable honey composition is stable when stored at temperatures between about 20° C. and about 35° C., e.g. at temperatures of about 35° C., for up to 15 days.

It is further preferred that the honey composition has a total activity against *Staphylococcus aureus* NZRM 87 (ATCC 9144), and expressed as equivalent % phenol, of at least about 19% phenol, preferably at least about 21% phenol, more preferably about 21-22% phenol, most preferably about 21.8% phenol.

In another aspect, the invention provides a topical preparation comprising a honey composition as defined above.

In still another aspect, the invention provides a tube containing a honey composition as defined above.

In still another aspect, the invention provides a jar containing a honey composition as defined above.

In still another aspect, the invention provides a honey composition as defined above for use as a medicament.

In yet another aspect the invention provides a method of treating or preventing a skin disorder, comprising administering to a patient in need thereof an effective amount of a bio-active honey, such as kanuka honey. Preferably the bio-active honey, such as kanuka honey, is administered topically. Preferably the kanuka honey is medical grade kanuka honey. Preferably the skin disorder is selected from the group consisting of acne, nappy rash and rosacea. Alternatively preferably the skin disorder is caused by herpes simplex virus 1 or 2. Still more preferably the skin disorder is rosacea. Alternatively preferably the skin disorder is genital herpes or oral herpes.

In yet another aspect the invention provides a method of treating or preventing a skin disorder, comprising administering to a patient in need thereof an effective amount of a honey composition as defined above. Preferably the honey is administered topically. It is also preferred that the honey composition is administered 1 to 5 times daily, e.g. twice daily.

In yet another aspect the invention provides the use of a honey composition as defined above for treating or preventing a skin disorder.

In yet another aspect the invention provides the use of a honey composition as defined above for the manufacture of a medicament for treating or preventing a skin disorder.

In yet another aspect the invention provides a honey composition as defined above for treating or preventing a skin disorder.

In yet a further aspect of the present invention there is provided a kit for treating or preventing a skin disorder, the kit comprising honey and glycerine together with instructions for treating or preventing the skin disorder.

Preferably the skin disorder is selected from the group consisting of acne, nappy rash and rosacea. Alternatively preferably the skin disorder is caused by herpes simplex virus 1 or 2. Still more preferably the skin disorder is rosacea. Alternatively preferably the skin disorder is genital herpes or oral herpes.

A honey composition as defined above is referred to herein as a "composition of the invention".

DETAILED DESCRIPTION

The present invention provides novel honey compositions, e.g. kanuka honey compositions, comprising honey and glycerine. The honey compositions of the invention are surprisingly stable even when stored at temperatures lower or higher than room temperature (e.g. even at normal household refrigeration temperatures). Advantageously, as shown in Example 2, compositions of the invention comprising kanuka honey retain their activities, as measured against *Staphylococcus aureus* NZRM 87 (ATCC 9144) and expressed as the equivalent % phenol.

The compositions of the invention are readily prepared by admixing honey, such as honey produced by bees who harvest the nectar of *Kunzea ericoides*, with glycerine. The preferred relative amounts of the honey and glycerine components range from about 85% w/w honey:15% w/w glycerine to about 95% w/w honey:5% w/w glycerine, preferably about 90% w/w honey:10% w/w glycerine, based on the total amount of ingredients. However, the invention also includes compositions comprising about 85% w/w honey:15% w/w glycerine, about 86% w/w honey:14% w/w glycerine, about 87% w/w honey:13% w/w glycerine, about 88% w/w honey:12% w/w glycerine, about 89% w/w honey:11% w/w glycerine, about 91% w/w honey:9% w/w glycerine, about 92% w/w honey:8% w/w glycerine, about 93% w/w honey:7% w/w glycerine, about 94% w/w honey:6% w/w glycerine or about 95% w/w honey:5% w/w glycerine, based on the total amount of ingredients. The composition is preferably substantially free of other components.

Although any honey can be used in a composition of the invention, bio-active honeys such as manuka honey or kanuka honey are particularly suitable for use in the compositions. The compositions of the invention provide the advantage that the biological activity of the honey is retained, even though the honey is diluted by admixing with glycerine. In some preferred embodiments of the invention, the biological activity of a composition of the invention (e.g. a composition comprising 90% w/w medical grade kanuka honey:10% w/w glycerine) has at least about 75%, more preferably at least about 80% and still more preferably at least about 85%, e.g. about 86-87% of the biological activity of 100% medical grade kanuka honey.

Those skilled in the art will realise that it is sometimes preferable to purify raw honey, for example where the honey is to be used in topical formulations, so that it is free from impurities that can cause undesirable inflammatory reactions in users. Thus, honey such as kanuka honey is preferably purified by filtration, e.g. through a 50 micron filter, and either pasteurisation or gamma irradiation, before being admixed with glycerine to form a composition of the invention. Preparative Example 1 describes how raw kanuka honey can be collected and purified.

Those skilled in the art will also understand that the glycerine used in the compositions of the invention can be any suitable glycerine, such as food grade glycerine (e.g. about 99.7+% pure food grade glycerine).

The honey compositions of the invention are stable when stored at temperatures below room temperature, e.g. between about 4° C. and about 10° C., e.g. between about 5° C. and about 9° C., e.g. between about 6° C. and about 8°

C., for up to 8 days, e.g. up to 7 days, up to 6 days, up to 5 days or up to 4 days. For example, the honey compositions of the invention can be stored at a temperature of about 4° C., for up to 8 days, e.g. up to 7 days, up to 6 days, up to 5 days or up to 4 days. It is also preferred that sugars present in the honey composition do not crystallise when the honey composition is stored at temperatures below room temperature, e.g. between about 4° C. and about 10° C., e.g. at a temperature of about 4° C., for up to 8 days, e.g. up to 7 days, up to 6 days, up to 5 days or up to 4 days.

It is further preferred that the honey composition is stable when stored at temperatures above room temperature, e.g. between about 20° C. and about 35° C., e.g. between about 21° C. and about 34° C., e.g. between about 22° C. and about 33° C., e.g. between about 23° C. and about 32° C., e.g. between about 24° C. and about 31° C., e.g. between about 25° C. and about 30° C., e.g. between about 26° C. and about 29° C., e.g. between about 27° C. and about 28° C., e.g. for up to 13 days, up to 10 days, up to 8 days or up to 5 days. For example, the honey compositions of the invention can be stored at a temperature of about 35° C., for up to 15 days, e.g. up to 13 days, up to 10 days, up to 8 days or up to 5 days.

The honey compositions of the invention are useful for the treatment of skin conditions such as acne, nappy rash, rosacea, and those caused by herpes simplex virus 1 or herpes simplex virus 2 (e.g. genital or oral herpes). For example, Example 3 describes a clinical trail of a composition of the invention (comprising 90% w/w medical grade kanuka honey and 10% w/w glycerine) for the treatment of rosacea. The primary outcome measure of the trial is the proportion of subjects who have a ≥2 improvement in an investigator-rated 7 point Rosacea Severity Score (RSS) at week 8 of the trial compared to baseline. The results show that 17.4% of patients in the control group have a more than or equal to two point change in RSS at week 8 from baseline. In contrast, 34.3% of patients in the group receiving a composition of the invention have a more than or equal to two point change in RSS at week 8 from baseline. (Relative risk composition of the invention versus control: 2.03 (95% CI 1.11 to 3.72), P=0.020.). Thus, the composition of the invention provides a clinically and statistically significant improvement in RSS versus control.

Those skilled in the art will understand that the honey compositions of the invention may also comprise one or more additional components, such as one or more bio-active components, e.g. drug compounds or components that are useful for treating a skin disorder. Such compositions comprise honey and glycerine in a ratio of about 85:15 to about 95:5 honey to glycerine, preferably about 90:10 honey to glycerine. In other words, a honey composition of the invention may be a base with which one or more additional component(s) is combined. It will be clear to those skilled in the art that, in such compositions, the ratio of honey to glycerine is about 85:15 to about 95:5 honey to glycerine. For example, a composition of the invention comprising honey and glycerine in a ratio 90:10 honey to glycerine may further comprise one or more drug compounds.

Those skilled in the art will also realise that the honey compositions of the invention can be administered to patients in a number of ways. For example, the compositions can be administered topically, e.g. for the treatment of skin conditions such as acne, nappy rash, rosacea, and those caused by herpes simplex virus 1 or herpes simplex virus 2 (e.g. genital or oral herpes). Alternatively, the compositions can be administered orally.

Typically, for topical treatment of skin disorders such as acne, rosacea, nappy rash, or those caused by herpes simplex virus 1 or herpes simplex virus 2 (e.g. genital or oral herpes), a composition of the invention is applied directly to the skin, in an amount sufficient to cover the area to be treated. A composition of the invention can be applied in this way up to 10 times per day, but more preferably about 1 to 5 times a day, and most preferably twice a day.

For the topical treatment of rosacea, the composition of the invention is applied to the affected area up to five times a day, preferably twice a day. Typically, the composition is applied for 30-60 minutes per application.

Alternatively, a kanuka honey is useful for the treatment of skin conditions and can be administered to patients topically, e.g. for the treatment of skin conditions such as acne, nappy rash, rosacea, or those caused by herpes simplex virus 1 or herpes simplex virus 2. Typically, for topical treatment of skin disorders such as acne, rosacea, nappy rash, or those caused by herpes simplex virus 1 or herpes simplex virus 2 (e.g. genital or oral herpes), a kanuka honey is applied directly to the skin, in an amount sufficient to cover the area to be treated. A kanuka honey can be applied in this way up to 10 times per day, but more preferably about 1 to 5 times a day, and most preferably twice a day. For the topical treatment of rosacea, the kanuka honey is applied to the affected area up to five times a day, preferably twice a day. Typically, the kanuka honey is applied for 30-60 minutes per application.

The compositions of the invention can be conveniently packaged into any suitable receptacle such as a tube, jar or other container, for use by consumers. Because of their stability, the compositions are suitable for storage at a range of temperatures in said receptacles.

The present invention also relates to devices and kits for treating skin disorders. Suitable kits comprise honey and glycerine sufficient for at least one treatment of at least one skin disorder, for separate, sequential or simultaneous use, together with instructions for performing the treatment/prevention. Preferably the skin disorder is selected from the group consisting of acne, nappy rash, rosacea, and those caused by herpes simplex virus 1 or herpes simplex virus 2 (e.g. genital or oral herpes).

The instructions for use of the kit and treating/preventing the skin disorder can be in the form of labelling, which refers to any written or recorded material that is attached to, or otherwise accompanies a kit at any time during its manufacture, transport, sale or use. For example, the term "labelling" encompasses advertising leaflets and brochures, packaging materials, instructions, audio or video cassettes, computer discs, as well as writing imprinted directly on kits.

Definitions

The term "kanuka honey" refers to honey produced by bees that harvest the nectar of *Kunzea ericoides*.

The term "medical grade kanuka honey" refers to honey produced by bees that harvest the nectar of *Kunzea ericoides*, which honey has been purified. Purification may be effected by filtration, e.g. through a 50 micron filter, and either pasteurisation or gamma irradiation.

The term "patient" includes human and non-human animals. Non-human animals include, but are not limited to, birds and mammals.

The terms "treatment" and the like refer to preventing, curing, delaying the onset of, or ameliorating a disease, disorder or condition, and/or reducing at least a symptom of such disease, disorder or condition, for example reducing pain and/or irritation and/or inflammation and/or swelling and/or redness and/or papules and/or pustules and/or flakiness.

Any reference or discussion in relation to prior art publications within this specification does not constitute an admission that such references form part of the common general knowledge in the art in any country or jurisdiction.

Throughout the description and the claims, the words "comprise", "comprising" and the like, are intended to be interpreted in an inclusive sense and not an exclusive or exhaustive sense, that is to say, "including, but not limited to".

EXAMPLES

The invention is further described with reference to the following examples. It will be appreciated that the invention as claimed is not intended to be limited in any way by these examples.

Preparative Example 1

Medical Grade Honey

Kanuka honey is sourced from kanuka (*Kunzea ericoides*) and processed to medical grade as follows:
Harvest Protocol:
Hives are located a minimum of 10 km from any intensive horticulture.
Hives have GPS location recorded.
All honey batches can be traced to site origin.
All hives are inspected by a certified apiarist.
Extraction Protocol:
All bees are removed prior to extraction.
Top and bottom bars of the frames are scraped and removed.
Wax cappings of the frames are pierced to eliminate wax contamination.
All frames are inspected to ensure absence of pollen cells.
All frames are inspected to ensure absence of brood cells.
Comb is pricked and honey extracted under pressure.
Honey is micro filtered to 50 microns.
Temperatures are maintained below 30° C. throughout production cycle.
Complies with New Zealand Food Safety Authority Risk assessment of harvesting and extraction process.
Assay Protocol/Honey Content:
Mono-floral purity >55%—(kanuka pollen count exceeds 55% under compound microscopic analysis).
Foreign matter <50 microns.
Crystallization <50 microns.
Microbiology <10 colony-forming units/g.
Hydroxymethylfurfural <10 mg/kg.
Para-dichlorobenzene: zero tolerance.
Antibiotic contamination: zero tolerance.
Water content <17%.
pH <3.9.
Sterilization
All honey is sterilized at apiary using high temperature pasteurization.

Example 1

Temperature Stability of Honey/Glycerine Composition

Two honey compositions are tested:
Formulation 1: 100% medical grade kanuka honey
Formulation 2 (prepared by admixing medical grade kanuka honey with glycerine): 90% w/w medical grade kanuka honey:10% w/w glycerine Samples of Formulation 1 and formulation 2 are stored at 4° C. for up to 8 days, 20° C. for up to 6 months and 35° C. for up to 15 days and their consistencies are then assessed. Results are shown in Table 1. The viscosity of formulation 1 decreases (relative to the formulation's viscosity at 20° C.) upon storage at 35° C., and increases (relative to the formulation's viscosity at 20° C.) upon storage at 4° C. The viscosity of formulation 2 is substantially similar upon storage at all temperatures (4° C., 20° C., 35° C.).

TABLE 1

Consistencies of honey compositions

| Formulation | Consistency at 4° C. | Consistency at 20° C. | Consistency at 35° C. |
| --- | --- | --- | --- |
| Formulation 1 | Hard, crystallised (more viscous) | Good | Runny (less viscous) |
| Formulation 2 | Good | Good | Good |

Example 2

Activity of Honey/Glycerine Composition

Four honey compositions are tested:
Formulation 1: 100% medical grade kanuka honey
Formulation 2 (prepared by admixing kanuka honey with glycerine): 90% w/w medical grade kanuka honey:10% w/w glycerine
Formulation 3 (prepared by admixing kanuka honey with Bio-Cert gel (Dehydroxanthan Gum Powder)): 40% w/w Bio-Cert gel (Dehydroxanthan Gum Powder): 60% w/w medical grade kanuka honey
Formulation 4 (prepared by admixing kanuka honey with glycerine): 40% w/w glycerine: 60% w/w medical grade kanuka honey.

Each formulation is tested for the Total Activity of the honey, i.e. the combination of the hydrogen peroxide ($H_2O_2$) found in ordinary honeys. This is conducted by application of the testing methods of Hills Labs and/or NZ Labs, that test for Total Activity (% of phenol), using the University of Waikato's Honey Assay Method (K. L. Allen, P. C. Molan, and G. M. Reid. A survey of the antibacterial activity of some New Zealand honeys. Journal of pharmacy and pharmacology 43.12 (1991): 817-822). The Total Activity is measured using *Staphylococcus aureus* NZRM 87 (ATCC 9144) and expressed as the equivalent % phenol.

Results are shown in Table 2.

TABLE 2

Activities of honey compositions

| Formulation | Total Activity (% phenol) |
| --- | --- |
| Formulation 1 | 25.2 |
| Formulation 2 | 21.8 |
| Formulation 3 | <8.2 |
| Formulation 4 | <8.2 |

Example 3

Clinical Trial for Rosacea

Study Design

Parallel group randomised controlled trial with assessor blinding.

Randomisation and Blinding:

Subjects and some staff at the study sites are not blinded to the treatment allocation. An independent investigator at each site remains blinded to the treatment allocation throughout the study and performs the RSS assessment.

Treatment allocation is randomised using a computer generated sequence. Subjects are randomised in a 1:1 ratio to one of the following regimens:
1. Application of a composition comprising topical kanuka honey and food grade glycerine combination, twice daily.
2. Application of a control cream (liquid paraffin and white soft paraffin topical emollient, Ultrabase®), twice daily.

Investigational Product:

The Investigational Product is topical medical grade kanuka honey and food grade glycerine (90% w/w honey: 10% w/w glycerine; a composition of the invention), packaged in 100 ml plain tubes. Subjects are provided with a sufficient amount of the Investigational Product, and apply an appropriate amount to the affected area twice daily for 30-60 minutes per application, for eight weeks. The treatment may then be removed with warm water as desired. Subjects may continue to use their usual medication, subject to the exclusion criteria. The plain 100 ml tubes are labelled according to Good Manufacturing Practice guidelines, for clinical trial use only.

Control Cream:

The control cream is a liquid paraffin and white soft paraffin topical emollient (Ultrabase®). Subjects apply topical control cream to the affected area twice daily for 30-60 minutes per application, for eight weeks.

The control cream is labelled according to Good Manufacturing Practice guidelines, for clinical trial use only.

Subject diaries are used to capture each subject's individual use of intervention, from Visit 1 until Visit 2. There are four trial sites Study Subjects:

136 patients aged 16 or over with a doctor's diagnosis of rosacea on the face. Subjects may be identified at the time of first presentation or, with their primary care practitioner's consent, from the practice database, or by public advertisement.

Inclusion Criteria:

Aged 16 or over at the time of enrolment

Baseline facial Rosacea severity score (RSS) of ≥2

Exclusion Criteria:

Requirement for topical or systemic corticosteroids, as judged by treating doctor Requirement for antibiotic therapy, as judged by treating doctor Known or suspected allergy to honey or control cream Any other condition which, at the investigator's discretion, it is believed may present a safety risk or impact the feasibility of the study or the study results Study Procedures and Treatments Recruitment and Consent:

Potentially eligible patients are identified at the time of presentation to their primary care practitioner, or via the practice database, or in public advertisement. Patients presenting with mild to moderate rosacea and who potentially meet inclusion and exclusion criteria, are offered the opportunity of taking part in the study.

Duration of Intervention:

Subjects apply their randomised intervention twice daily for eight weeks. They attend for 3 visits in total; Baseline, Visit 2 and Visit 3.

Study Visits:

Consent, screening, baseline measurements and randomisation are completed at Visit 1 (Week 0). The response is assessed at Visit 2 (Week 2) and Visit 3 (Week 8).

TABLE 3

Schedule of Assessments

| | Visit number | | |
|---|---|---|---|
| | Visit 1 | Visit 2 | Visit 3 |
| | Time point | | |
| | Week 0 Day 1 | Week 2 Day 14 | Week 8 Day 56 |
| Informed consent | x | | |
| Eligibility criteria checked | x | | |
| Demographics and medical history | x | | |
| Randomisation | x | | |
| Administer DLQI | x | x | x |
| Administer RSS | x | x | x |
| Subject severity VAS completion | x | x | |
| Subject rated improvement VAS completion | | x | x |
| Provision of subject diary | x | | |
| Collection of subject diary | | x | |
| Safety monitoring | x | x | x |

[a] RSS is administered by the blinded investigator
[b] Severity VAS is completed daily from Visit 1 until Visit 2, within the subject diary.
DLQI: Dermatology Life Quality Index
VAS: Visual Analogue Score Visit 1 (Baseline Visit):

Recruitment and consent procedures are completed. A second investigator blinded to treatment allocation performs the baseline RSS. The subject completes a DLQI and VAS for overall rosacea severity. The subject is randomised into the study, and the procedure for applying the allocated treatment is explained to the subject. A 'subject diary' is provided to the subject and they are instructed on how to complete it. The subject enters information daily on application of the treatment and completes a subjective assessment of Rosacea severity by VAS, from the baseline visit until the Week 2 visit.

Visit 2:

The subject's diary is collected at visit 2 (week 2) and reviewed for completeness. The subject is asked if they have experienced any adverse effects, which will be recorded and reported as per the 'Safety Monitoring' section. The subject completes a Rosacea severity VAS and the DLQI. Narrative feedback is also recorded. The subject completes the subject rated improvement VAS. The second investigator blinded to treatment allocation performs the RSS (this is the same investigator that performed the original assessments).

Visit 3 (Final Visit):

The subject is asked if they have experienced any adverse effects, which will be recorded and reported as per the 'Safety Monitoring' section. The subject completes a Rosacea severity VAS and the DLQI. Narrative feedback is also recorded. The subject completes the subject rated improvement VAS. The second investigator blinded to treatment allocation performs the RSS1 (this is the same investigator that performed the original assessments).

Study Visit Windows:

Each visit is conducted as close as possible to the scheduled date. If this is not possible then Visit 2 may be conducted on Day 14±3 days, and Visit 3 may be conducted on Day 56±7 days.

Post Trial Handling:

Subjects revert to usual care under their primary care practitioner.

Outcome Measures

Primary:

The proportion of subjects who have a ≥2 improvement in investigator-rated 7 point Rosacea Severity Score (RSS) at week 8 compared to baseline.

Secondary:

Change in subject-rated rosacea related quality of life, using the Dermatology Life Quality Index (DLQI), at weeks 2 and 8 compared to baseline.

Subject-rated global rosacea improvement using a Visual Analogue Score (VAS) at weeks 2 and 8

Change in subject-rated global rosacea severity using Visual Analogue Score (VAS) at week 2 compared to baseline.

Change in investigator-rated 7 point RSS at Week 2 and Week 8 compared to baseline.

Daily self-reported use (applications per day).

Weekly self-reported global rosacea severity (VAS scale).

Withdrawals due to worsening of rosacea.

lines. AEs and SAEs will be followed up until resolution, or until judged permanent.

Serious Adverse Events (SAEs):

For the purposes of this study the following events are considered to be SAEs:

Death

Life-threatening event

Permanently disabling or incapacitating event

Hospitalisation or prolongation of hospitalisation. Hospitalisation for the purposes of SAE reporting is defined as an admission to hospital and does not include a presentation to the Emergency Department followed by discharge without admission or an admission for elective reasons Any event considered serious by the study investigator Reporting of SAEs to the Ethics Committee takes place in accordance with the conditions of ethical approval for the study.

Pregnancy itself is not regarded as an SAE. Any congenital anomaly or birth defect is considered to be an SAE.

General Health Care

Participants receive usual general practitioner care during the study.

Power and Statistical Methods

Sample Size and Study Power:

136 participants allows for a 10% drop-out rate. Analysis of 124 participants provides at least 80% power at 5% significance to detect a 25% difference in response rates between the groups.

TABLE 4

Trial Results

Primary outcome

| | |
|---|---|
| Proportion with a ≥2 improvement in RSS at week 8 compared to baseline | Relative risk composition of the invention versus control: 2.03 (95% CI 1.11 to 3.72), P = 0.020 |

Secondary outcomes

| | |
|---|---|
| Subject-rated rosacea improvement using a VAS at week 2 | composition of the invention minus control 9.1 (3.5 to 14.7), P = 0.002 |
| Subject-rated rosacea improvement using a VAS at week 8 | composition of the invention minus control 12.3 (5.7 to 18.9), P < 0.001 |
| Change in subject-rated rosacea severity using VAS at week 2 compared to baseline | composition of the invention minus control −8.2 (−13.9 to −2.5), P = 0.005 |
| Change in RSS at week 2 compared to baseline | composition of the invention minus control, Hodges-Lehman estimate, −1 (−1 to 0), P = 0.03 |
| Change in RSS at week 8 compared to baseline | composition of the invention minus control, Hodges-Lehman estimate, −1 (−1 to 0), P = 0.005 |
| Withdrawals due to worsening | 9/69 (13.0%) in the control group, 3/68 (4.4%) in the composition of the invention group |

Safety Monitoring

Adverse Events:

An adverse event is any untoward medical occurrence in a study subject temporally associated with participation in the trial and the administration of study medication, whether or not considered related to the medicine. An adverse event can therefore be any unfavourable and unintended sign, symptom or disease temporally associated with the use of the study treatment.

Adverse event data is collected and analysed with efficacy data at the end of the study. Serious adverse events are notified to the ethics committee according to standard guide- References

[1] Elewski, Boni E., Alan B. Fleischer Jr and David M. Pariser "A comparison of 15% azelaic acid gel and 0.75% metronidazole gel in the topical treatment of papulopustular rosacea: results of a randomized trial" Archives of dermatology 139.11 (2003): 1444.

[2] Finlay, A. Y. and Khan, G. K. "Dermatology Life Quality Index (DLQI)—a simple practical measure for routine clinical use" Clin Exp Dermatol. 1994; 19: 210-216.

Where the foregoing description reference has been made to integers having known equivalents thereof, those equivalents are herein incorporated as if individually set forth.

Although the invention has been described in connection with specific preferred embodiments, it should be understood that the invention as claimed should not be unduly limited to such specific embodiments.

It is appreciated that further modifications may be made to the invention as described herein without departing from the spirit and scope of the invention.

INDUSTRIAL APPLICABILITY

The invention relates to compositions comprising honey and glycerine, methods for preparing such compositions and their use for the treatment or prevention of skin diseases such as acne, rosacea or nappy rash.

The invention claimed is:

1. A method of treating a human suffering from rosacea, herpes simplex virus 1, and/or herpes simplex virus 2, the method consisting essentially of administering to the human suffering from rosacea, herpes simplex virus 1, and/or herpes simplex virus 2 a therapeutically effective amount of a composition consisting essentially of from about 85% w/w to about 95% w/w kanuka honey and from about 5% w/w to about 15% w/w glycerine.

2. A method as claimed in claim 1, wherein the human is suffering from herpes simplex virus 1 and/or herpes simplex virus 2.

3. A method as claimed in claim 1, wherein the human is suffering from rosacea.

4. A method as claimed in claim 1, wherein the composition is administered topically 1 to 5 times a day.

5. A method as claimed in claim 2, wherein the composition is administered topically 1 to 5 times a day.

6. A method as claimed in claim 3, wherein the composition is administered topically 1 to 5 times a day.

7. A method as claimed in claim 1, wherein the composition is administered topically twice a day.

8. A method as claimed in claim 2, wherein the composition is administered topically twice a day.

9. A method as claimed in claim 3, wherein the composition is administered topically twice a day.

10. A method as claimed in claim 1, wherein the honey is medical grade kanuka honey.

11. A method as claimed in claim 2, wherein the honey is medical grade kanuka honey.

12. A method as claimed in claim 3, wherein the honey is medical grade kanuka honey.

13. A method as claimed in claim 1, wherein the composition consists essentially of about 90% w/w honey and about 10% w/w glycerine.

14. A method as claimed in claim 2, wherein the composition consists essentially of about 90% w/w honey and about 10% w/w glycerine.

15. A method as claimed in claim 3, wherein the composition consists essentially of about 90% w/w honey and about 10% w/w glycerine.

16. A method as claimed in claim 1, wherein the composition is stable when stored at temperatures below or above room temperature.

* * * * *